United States Patent
Kaku et al.

(10) Patent No.: US 9,555,028 B2
(45) Date of Patent: Jan. 31, 2017

(54) DRUG FOR PREVENTING/TREATING OCULAR DISEASE

(71) Applicants: JAPAN BIO PRODUCTS CO., LTD., Shibuya-ku, Tokyo (JP); THE DOSHISHA, Kyoto-shi, Kyoto (JP)

(72) Inventors: Taiichi Kaku, Tokyo (JP); Yoshiharu Kadota, Osaka (JP); Shumpei Yamaguchi, Tokyo (JP); Takahiro Nakamura, Kyotanabe (JP); Masashi Akitsu, Tokyo (JP)

(73) Assignees: JAPAN BIO PRODUCTS CO., LTD, Shibuya-Ku (JP); THE DOSHISHA, Kyoto-Shi (JP)

( * ) Notice: Subject to any disclaimer, the term of this patent is extended or adjusted under 35 U.S.C. 154(b) by 0 days.

(21) Appl. No.: 14/413,455

(22) PCT Filed: Apr. 5, 2013

(86) PCT No.: PCT/JP2013/060460
§ 371 (c)(1),
(2) Date: Apr. 14, 2015

(87) PCT Pub. No.: WO2014/010281
PCT Pub. Date: Jan. 16, 2014

(65) Prior Publication Data
US 2015/0148350 A1    May 28, 2015

(30) Foreign Application Priority Data
Jul. 9, 2012    (JP) ................................ 2012-153729

(51) Int. Cl.
| A61K 31/50 | (2006.01) |
| A61K 31/4985 | (2006.01) |
| A61K 38/05 | (2006.01) |
| A61K 38/12 | (2006.01) |
| A61K 9/00 | (2006.01) |
| A61K 9/08 | (2006.01) |

(52) U.S. Cl.
CPC ......... *A61K 31/4985* (2013.01); *A61K 9/0048* (2013.01); *A61K 9/08* (2013.01); *A61K 38/05* (2013.01); *A61K 38/12* (2013.01)

(58) Field of Classification Search
CPC .. A61K 9/0019; A61K 8/375; A61K 2800/75; A61K 31/22; A61K 36/02; A61K 36/185; A61K 36/28; A61K 36/355; A61K 36/61; A61K 36/738; A61K 47/10; A61K 47/14; A61K 47/44; A61K 8/0208; A61K 8/345
See application file for complete search history.

(56) References Cited

U.S. PATENT DOCUMENTS

| 6,635,620 B1 * | 10/2003 | Yagi ..................... C07D 207/16 514/16.5 |
| 2006/0111356 A1 | 5/2006 | Yagi et al. |
| 2008/0075787 A1 * | 3/2008 | Hibino ................. A61K 9/0048 424/583 |
| 2008/0306079 A1 * | 12/2008 | Yagi ........................ A61K 9/06 514/249 |

FOREIGN PATENT DOCUMENTS

| CN | 101111253 A | 1/2008 |
| JP | H11-21295 A | 1/1999 |
| JP | 2001-288106 A | 10/2001 |
| JP | 2003-313127 A | 11/2003 |
| JP | 3969831 B2 | 9/2007 |
| JP | 4253161 B2 | 4/2009 |
| JP | 4601118 B2 | 12/2010 |
| KR | 10-2007-0094600 | 9/2007 |

OTHER PUBLICATIONS

Javadi et al, Dry Eye Syndrome, J Ophthalmic Vis Res 2011; 6 (3): 192-198.*
Argueso, P. et al., "Analysis of Human Ocular Mucus: Effects of Neuraminidase and Chitinase Enzymes", Cornea, vol. 17, No. 2 (Mar. 1998), pp. 200-207.
Musumeci, M. et al., "Acidic Mammalian Chitinase in Dry Eye Conditions", Cornea, vol. 28, No. 6 (Jul. 2009), pp. 667-672.
"The Merck Manual 17th Edition", NIKKEI BP (Dec. 10, 1999), pp. 719-720 (English and Japanese).
Houston, D.R. et al., "Structure-Based Exploration of Cyclic Dipeptide Chitinase Inhibitors", J. Med. Chem., vol. 47, No. 23 (Nov. 4, 2004), pp. 5713-5720.
Takahiro Nakamura et al., "JBP485 promotes tear and mucin secretion in ocular surface epithelia," Scientific Reports, vol. 5, May 21, 2015, XP055229723. (From ESR Dec. 7, 2015.).
L. Modis Jr. et al., "Dry eye diagnosis and management," Expert Review of Opthalmology, Future-Drugs, XX, vol. 6, No. 1, Feb. 2011, pp. 67-79, XP009187330. (From ESR Dec. 7, 2015.).
Akira Yagi, et al. "Effect of cyclo (trans-4-L-hydroxyprolyl-L-serine) from hydrolysate of human placenta on baby hamster kidney," Naturat Medicines, vol. 52, No. 2, Dec. 31, 1998, p. 156-p. 159.

(Continued)

*Primary Examiner* — Jean Cornet
(74) *Attorney, Agent, or Firm* — Andrews Kurth Kenyon LLP

(57) ABSTRACT

The present invention relates to a medicament for preventing or treating an ocular disease comprising cyclo-trans-4-L-hydroxyprolyl-L-serine as an active ingredient, a medicament for preventing or treating dry eye comprising the compound as an active ingredient, and, in particular, a medicament for preventing or treating dry eye having an action of enhancing mucin secretion and an action of enhancing repair of ocular tissue damage caused by dry eye.

4 Claims, 5 Drawing Sheets

(56) References Cited

OTHER PUBLICATIONS

Ke-Xin Liu, et al. "Hydroxyprolylserine Derivatives JBP923 and JBP485 Exhibit the Antihepatitis Activities after Gastrointestinal Absorption in Rats," The Journal of Pharmacology and Experimental Therapeutics, vol. 294, No. 2, Dec. 31, 2000, p. 510-p. 515.

Cai Rongrong, "Mucins and dry eye," Chin Ophthal Res, vol. 26, No. 11, Nov. 30, 2008, p. 877-p. 880.

* cited by examiner

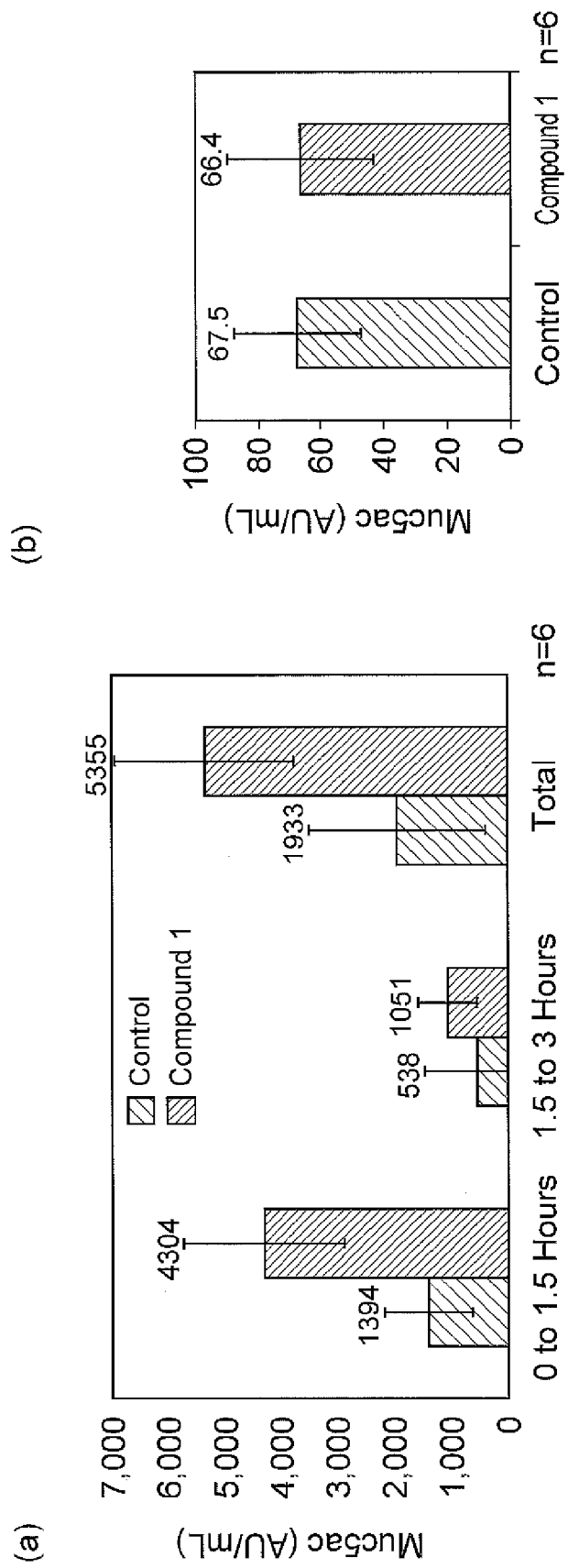

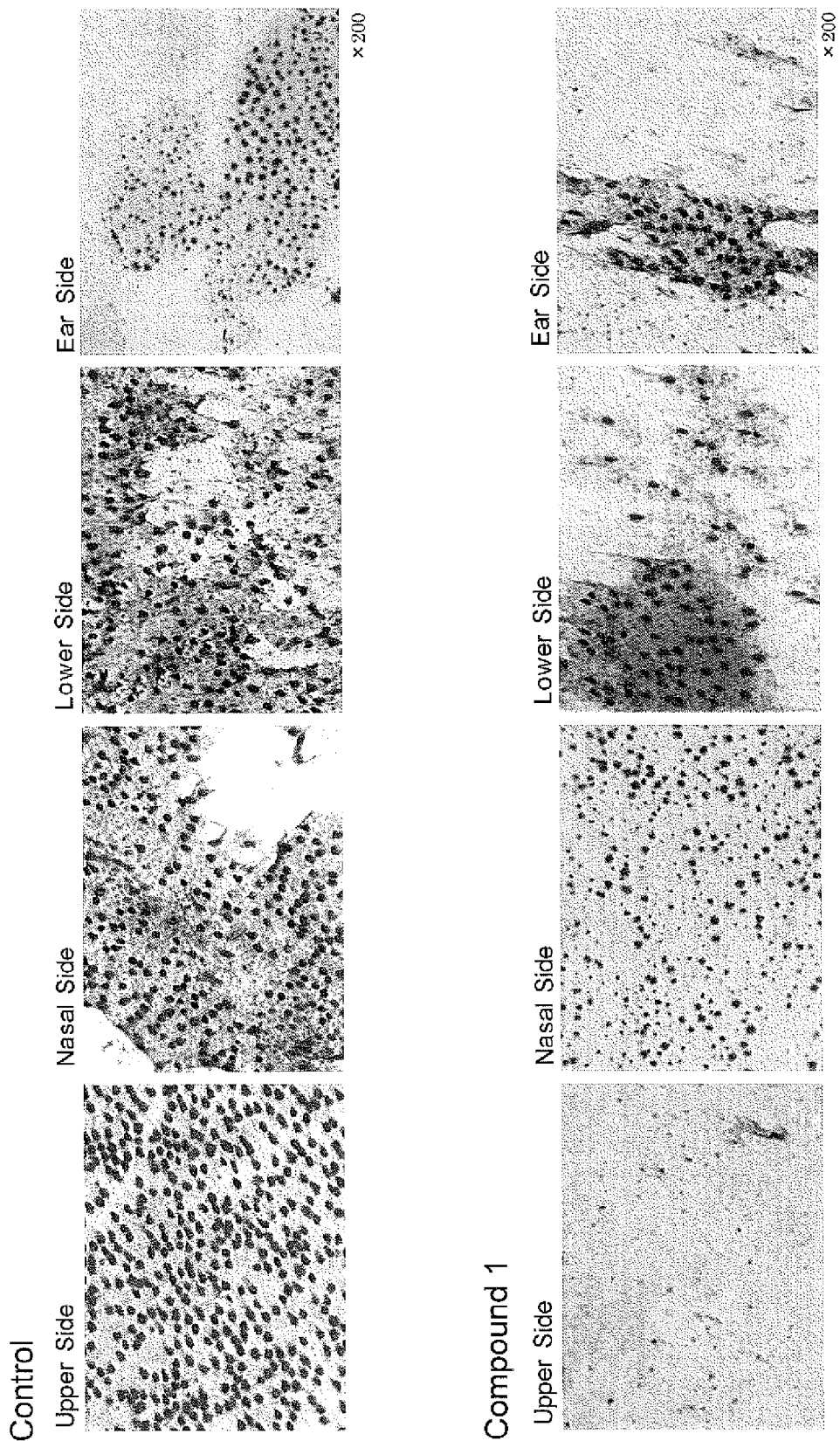

DRUG FOR PREVENTING/TREATING OCULAR DISEASE

CROSS-REFERENCE TO RELATED APPLICATIONS

This is a national phase application based on the PCT International Patent Application No. PCT/JP2013/060460 filed Apr. 5, 2013, claiming priority to Japanese Patent Application No. 2012-153729 filed Jul. 9, 2012, the entire contents of both of which are incorporated herein by reference.

TECHNICAL FIELD

The present invention relates to a medicament for preventing or treating an ocular disease. The present invention relates in particular to a medicament for preventing or treating dry eye and a mucin secretion enhancer.

BACKGROUND ART

Dry eye is a chronic disease, which is caused by various factors, on lacrimal fluid and corneal/conjunctival epithelium and is an ocular disease accompanied by ocular discomfort and dysfunction. The number of dry eye patients in Japan is estimated to be 20 million. Examples of a medicament for treating dry eye are limited to sodium hyaluronate eye drops and/or administration of artificial lacrimal fluid, but a medicament comprising diquafosol sodium or rebamipide as an active ingredient and having an action of enhancing secretion of mucin from a conjunctival tissue have become commercially available. Among the mucins, Muc5ac is a protein that is secreted from goblet cells of an ocular conjunctival tissue, and is an important component constituting lacrimal fluid. A decrease in the amount of mucin is one of factors causing dry eye.

Meanwhile, cyclo-trans-4-L-hydroxyprolyl-L-serine is a hydroxyproline derivative, and has been known to have cell proliferation and cell protection actions (Patent Literature 1) and to be effective in preventing or treating allergic and inflammatory diseases (Patent Literatures 2 and 3).

CITATION LIST

Patent Literature

[Patent Literature 1] Japanese Patent No. 3969831
[Patent Literature 2] Japanese Patent No. 4253161
[Patent Literature 3] Japanese Patent No. 4601118

SUMMARY OF INVENTION

Technical Problem

It is an object of the present invention to provide a novel medicament for preventing or treating an ocular disease, in particular to provide a medicament for preventing or treating dry eye, and especially to provide a medicament for preventing or treating dry eye having an action of enhancing mucin secretion and an action of enhancing repair of ocular tissue damage caused by dry eye.

Solution to Problem

The present inventors have found that cyclo-trans-4-L-hydroxyprolyl-L-serine (hereinafter, also referred to as Compound 1) enhances mucin secretion in a concentration-dependent manner. The mucin-secretion-enhancing action of Compound 1 totally differs from known actions of Compound 1, and such an action is an unexpected result.

The present inventors have further found that Compound 1 also enhances repair of ocular tissue damage caused by dry eye. Although Patent Literature 1 discloses that Compound 1 is useful in tissue repair and regeneration, Patent Literature 1 only discloses a liver protection action and is silent on ocular tissue repair. The liver and eyes are totally different tissues and their repair/regeneration mechanisms are also totally different. Thus, the action of Compound 1 on enhancing repair of ocular tissue damage caused by dry eye is an unexpected effect.

In view of the above findings, the present inventors have completed the present invention. Specifically, the present invention provides a medicament for preventing or treating dry eye comprising Compound 1 as an active ingredient. In particular, the present invention provides a medicament for preventing or treating dry eye comprising Compound 1 as an active ingredient, wherein dry eye is caused by a decrease in an amount of mucin. The medicament for preventing or treating dry eye according to the present invention also enhances repair of ocular tissue damage caused by dry eye.

The present invention further provides a mucin secretion enhancer comprising Compound 1 as an active ingredient.

The present invention further provides the following aspects (1) to (12):

(1) a method for preventing or treating dry eye, comprising administering to a patient an effective amount of cyclo-trans-4-L-hydroxyprolyl-L-serine;

(2) a method for preventing or treating dry eye caused by a decrease in an amount of mucin, comprising administering to a patient an effective amount of cyclo-trans-4-L-hydroxyprolyl-L-serine;

(3) a method for enhancing mucin secretion, comprising administering to a patient an effective amount of cyclo-trans-4-L-hydroxyprolyl-L-serine;

(4) a method for enhancing repair of ocular tissue damage caused by dry eye, comprising administering to a patient an effective amount of cyclo-trans-4-L-hydroxyprolyl-L-serine;

(5) cyclo-trans-4-L-hydroxyprolyl-L-serine for use in preventing or treating dry eye;

(6) cyclo-trans-4-L-hydroxyprolyl-L-serine for use in preventing or treating dry eye caused by a decreased in an amount of mucin;

(7) cyclo-trans-4-L-hydroxyprolyl-L-serine for use in enhancing mucin secretion;

(8) cyclo-trans-4-L-hydroxyprolyl-L-serine for use in enhancing repair of ocular tissue damage caused by dry eye;

(9) use of cyclo-trans-4-L-hydroxyprolyl-L-serine for the manufacture of a medicament for preventing or treating dry eye;

(10) use of cyclo-trans-4-L-hydroxyprolyl-L-serine for the manufacture of a medicament for preventing or treating dry eye caused by a decrease in an amount of mucin;

(11) use of cyclo-trans-4-L-hydroxyprolyl-L-serine for the manufacture of a mucin secretion enhancer; and

(12) use of cyclo-trans-4-L-hydroxyprolyl-L-serine for the manufacture of an enhancer for repair of ocular tissue damage caused by dry eye.

Advantageous Effects of Invention

The present invention provides a novel medicament for preventing or treating an ocular disease, and in particular, provides a medicament for preventing or treating dry eye, a medicament for preventing or treating dry eye caused by a decrease in an amount of mucin, and a medicament for preventing or treating dry eye which enhances repair of ocular tissue damage caused by dry eye and a mucin secretion enhancer.

BRIEF DESCRIPTION OF DRAWINGS

FIG. 4 shows graphs illustrating an effect of Compound 1 on enhancing secretion of Muc5ac in vivo. FIG. 4(a) shows the results of quantifying secreted Muc5ac in a culture supernatant by ELISA. The term "Total" means a total amount of Muc5ac that was quantified from 0 to 1.5 hours and from 1.5 to 3 hours. FIG. 4(b) shows the results of quantifying an amount of Muc5ac protein in a conjunctival tissue.

FIG. 5 shows the results of PAS staining demonstrating an effect of Compound 1 to enhance secretion of Muc5ac in vivo.

DESCRIPTION OF EMBODIMENTS

Figure 1:
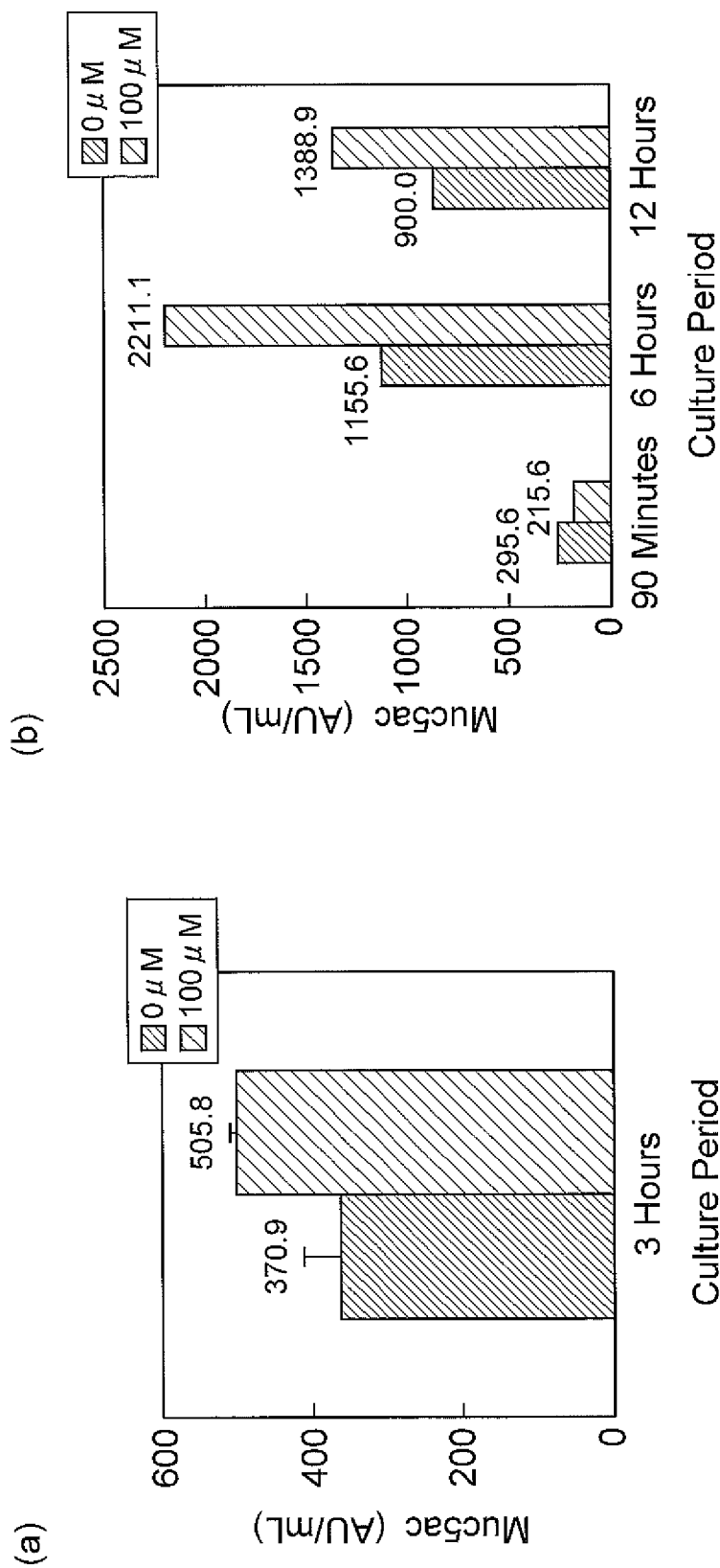
FIG. 1 shows graphs illustrating an amount of Muc5ac in a culture supernatant of a conjunctival tissue in the presence or absence of Compound 1. After the tissue was cultured for an indicated time in a Hanks' balanced salt solution (hereinafter, also referred to as an HBSS) containing an indicated concentration of Compound 1, the culture supernatant was collected and the amount of Muc5ac was quantified by ELISA.

Hereinafter, preferable embodiments of the present invention will be described in detail. The present invention, however, is not limited to these Embodiments.

The present invention provides a medicament for preventing or treating dry eye comprising Compound 1 as an active ingredient. Administering the medicament for preventing or treating dry eye can decrease probabilities that normal eyes would suffer from dry eye and can decrease a symptom of a patient suffering from dry eye.

As used herein, Compound 1 is a compound represented by the following chemical formula (1). The form of Compound 1 may be a free form or a pharmacologically acceptable salt thereof may be formed.

(1)

Examples of a process for producing Compound 1 include, but are not limited to, processes disclosed in Patent Literatures 1 and 3.

A medicament for preventing or treating dry eye comprising Compound 1 as an active ingredient of this embodiment may be used by mixing with pharmacologically essential components such as suitable pharmaceutically acceptable additives. Examples of such additives include carriers, excipients, pH modifiers, and diluents.

A dosage form of the above medicament for preventing or treating dry eye is not particularly limited, but it is preferable to prepare a pharmaceutical preparation having a dosage form such as eye drops, internal medicines or injections. The content of Compound 1 in the above preparation may be suitably adjusted by those skilled in the art, and examples of a method for preparing the above preparation include, but are not particularly limited to, known methods.

An effective dosage and dosing schedule of the medicament for preventing or treating dry eye may be suitably determined by those skilled in the art depending on, for example, an administration method, conditions, weight, and age of a patient.

Because Compound 1 possesses a mucin-enhancing action, the compound is particularly effective as a medicament for preventing or treating dry eye caused by a decrease in an amount of mucin. Note that as used herein, the mucin is not particularly limited and examples of the mucin include Muc5ac.

In addition, a medicament for preventing or treating dry eye of the present invention also enhances repair of ocular tissue damage caused by dry eye. In view of this, the medicament for preventing or treating dry eye of this embodiment can enhance wound healing of ocular tissue damage caused by dry eye.

The ocular tissue is not particularly limited as long as it is a tissue constituting an eye, and is preferably a cornea or a conjunctiva and more preferably a corneal epithelial tissue or a conjunctival epithelial tissue.

The present invention also provides a mucin secretion enhancer comprising Compound 1 as an active ingredient. Administering the mucin secretion enhancer comprising Compound 1 as an active ingredient can increase secretion of mucin that is a component of lacrimal fluid.

EXAMPLES

The following specifically describes the present invention by referring to Examples, but the present invention is not limited to these Examples.

Example 1

Effect of Compound 1 on Muc5ac Secretion

In order to examine an effect of Compound 1 on an amount of Muc5ac secretion, ex vivo experiments were carried out using a conjunctival tissue from a white rabbit (Slc:JW/CSKSlc:NZW strain).

Specifically, a trephine with a diameter of 3 mm was used to sample a conjunctival tissue from a white rabbit. Next, the tissue sample was soaked in an HBSS containing 100 µM of Compound 1 for 90 minutes, 3 hours, 6 hours, or 12 hours. The conjunctival tissue of the control group was soaked in an HBSS having a physiological saline with a volume equal to that of Compound 1. After the conjunctival tissue was soaked for a predetermined time, its culture supernatant was collected. For each group, the experiment was performed at n=5.

The amount of Muc5ac included in the culture supernatant was detected using the following assay.

Assay for Muc5ac Secretion (ELISA Assay)

First, the culture supernatant of the conjunctival tissue of the control group was diluted using an HBSS, and a standard curve was prepared at a Muc5ac concentration of 500, 250, 125, 62.5, 31.25, 15.63, and 7.81 AU/mL (AU represents an arbitrary unit). The sample solutions were diluted with an HBSS in such a manner that absorbance at a wavelength of 450 nm was fitted within a range of the absorbance of the standard curve at a wavelength of 450 nm. Next, the solutions for the standard curve, the sample solutions for the test group, and the sample solutions for the control group were added to a 96-well microplate (#3590, manufactured by Corning Incorporated) at 100 μL/well, and were incubated overnight at 40° C. For each sample, the measurement was performed at n=2.

After the solutions for the standard curve and the sample solutions were removed, 200 μL of washing buffer was used to wash the wells three times. The washing buffer (hereinafter, also referred to as a TBST solution) was prepared by adding Tween-20 at a final concentration of 0.05% to Tris buffered saline (pH 7.6).

Then, 200 μL of blocking buffer (1% bovine serum albumin-containing TBST solution) was added to each well, and the plate was incubated at room temperature for 1 hour. After the blocking buffer had been removed, a primary antibody (an anti-human Muc5ac antibody, manufactured by NeoMarkers, Inc.; Clone 45M1) solution, which was 100-fold diluted with the blocking buffer, was added to the plate at 100 μL/well, and the plate was incubated at room temperature for 1 hour. After the primary antibody solution was removed, 200 μL of the washing buffer was used to wash the wells three times.

Then, a secondary antibody (an HRP-labelled sheep anti-mouse IgG antibody, manufactured by GE Healthcare, Inc.) solution, which was 2000-fold diluted with the blocking buffer, was added to the plate at 100 μL/well, and the plate was incubated at room temperature for 1 hour. After the secondary antibody solution was removed, 200 μL of the washing buffer was used to wash the wells three times.

In order to quantify the Muc5ac content in each sample, 100 μL of 3,3',5,5'-tetramethylbenzidine was added to each well and the plate was incubated for coloring at room temperature for 30 minutes; and then 100 μL of 0.5 M sulfuric acid solution was added to each well to stop the reaction. Next, a microplate reader was used to measure the absorbance of each well at a wavelength of 450 nm. The Muc5ac content in each sample was calculated using the standard curve.

As shown in FIG. 1(a), when the conjunctival tissue was cultured in the presence of Compound 1 for 3 hours, the amount of Muc5ac increased compared with the case that the conjunctival tissue was cultured in the absence of Compound 1. In addition, as shown in FIG. 1(b), an increase in an amount of Muc5ac in the presence of Compound 1 was observed when the conjunctival tissue was cultured under in presence of Compound 1 for 6 and 12 hours. At 6 hours of culturing, a difference in the amount of Muc5ac between the presence and absence of Compound 1 is most prominent.

Example 2

Concentration Dependence on Compound 1 with Respect to Muc5ac Secretion

A trephine with a diameter of 3 mm was used to sample a conjunctival tissue from a white rabbit, and the tissue was soaked in an MSS containing 0, 1, 10, or 100 μM of Compound 1. The conjunctival tissue of the control group was soaked in an HBSS having a physiological saline solution with a volume equal to that of Compound 1. After the conjunctival tissue was soaked for 6 hours, its culture supernatant was collected. For each group, the experiment was performed at n=5.

The amount of Muc5ac included in the culture supernatant was detected using the same ELISA assay as in Example 1.

Figure 2:
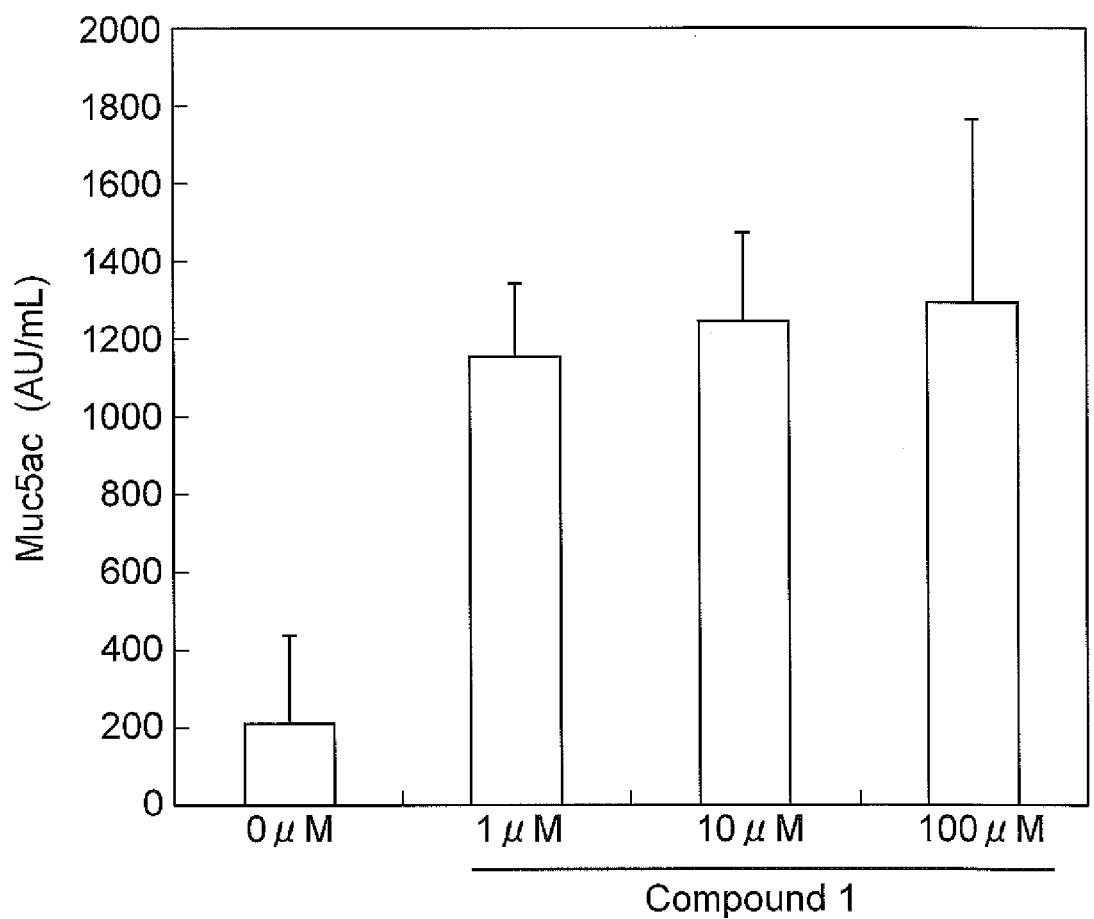
FIG. 2 is a graph showing concentration dependence on Compound 1 with respect to an amount of Muc5ac in a culture supernatant of a conjunctival tissue. After the tissue was cultured for 6 hours in an HBSS containing an indicated concentration of Compound 1, the culture supernatant was collected and the amount of Muc5ac was quantified by ELISA.

As shown in FIG. 2, the amount of Muc5ac included in the culture supernatant increased depending on the concentration of Compound 1 in the HBSS.

The above results demonstrated that Compound 1 has an action of enhancing mucin secretion from a conjunctival tissue.

Example 3

Wound Healing Effect of Compound 1 on Corneal Epithelial Tissue

In order to examine an wound healing effect of Compound 1 on an corneal epithelial tissue, in vivo experiments were carried out using white rabbits (Slc:JW/CSKSlc:NZW strain).

Specifically, a trephine with a diameter of 8 mm was used to create a wound on a corneal epithelial tissue of a white rabbit. From the day of creating the wound, the test group was subjected to instillation administration of a solution containing 100 μM of Compound 1, which had been dissolved in a physiological saline solution, at a dosage of 30 μL to 50 μL/dose 4 times per day. The control group was subjected to instillation administration of a physiological saline solution at a dosage of 30 μL to 50 μL/dose 4 times per day. For each group, the experiment was performed at n=5.

In order to determine the area of the wound on the corneal epithelial tissue, a physiological saline solution and a fluorescein test paper were used to perform fluorescein staining of the corneal epithelial tissue; and a time course change in the area of the wound on the corneal epithelium was observed while its photographs were taken. The wound area was image-processed using Image J software and was statistically analyzed.

Figure 3:
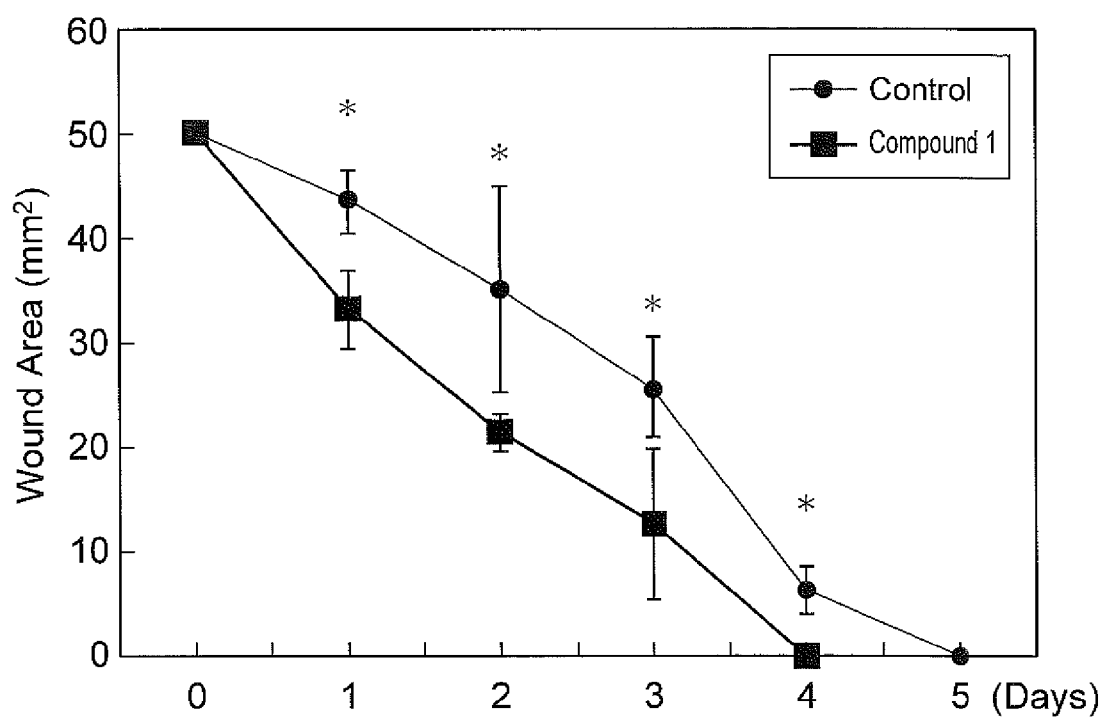
FIG. 3 is a graph showing a time course of a wound healing effect of Compound 1 on a corneal epithelial tissue. The asterisks indicate a significant difference ($p<0.01$).

The results of the statistical analysis of the wound area as determined by the above procedure were shown in FIG. 3. The wound area of the Compound 1 administration group was smaller from Day 1 of the administration than that of the control group, and the results of statistical analysis using t-test demonstrated that their difference was significant ($p<0.01$). In addition, the time required for complete cure of the wound was 5 days for the control group, but the time required was 4 days for the Compound 1 administration group. Hence, it was demonstrated that Compound 1 has an action of enhancing wound healing of a corneal epithelial tissue.

Example 4

Compound 1 Enhances Secretion of Muc5ac In Vivo

In order to examine whether or not Compound 1 enhances Muc5ac secretion, in vivo experiments were carried out using white rabbits (Slc:JW/CSKSlc:NZW strain).

Specifically, the right eye of a white rabbit was subjected to instillation administration of a solution containing 100 μM of Compound 1, which had been dissolved in a physiological saline solution, at a dosage of 30 μL to 50 μL/dose 4 times per day. The left eye was subjected to instillation administration of a physiological saline solution as a control at a dosage of 30 μL to 50 μL/dose 4 times per day. For each group, the experiment was performed at n=6.

After 3 days with the above administration, each white domestic rabbit was euthanized and its conjunctival tissue was sampled using a trephine with a diameter of 5 mm. The sample was soaked in an HBSS; its culture supernatant was collected after an hour and a half; and further, after 3 hours, its culture supernatant and conjunctival tissue were collected. The amount of Muc5ac included in the culture supernatant was quantified using the same ELISA assay as in Example 1. The results are shown in FIG. 4a. It was revealed that compared with that of the control group, the amount of Muc5ac included in the culture supernatant of the conjunctival tissue collected from the Compound 1 administration group was remarkably high.

Meanwhile, 150 μL of SDS(−) RIPA lysis buffer (manufactured by Nacalai Tesque, Inc.) was added to the conjunctival tissue collected, and the tissue was soaked and incubated at 4° C. for 30 minutes, followed by homogenization. Then, the homogenate was centrifuged at 4° C. and 15000 rpm for 10 minutes, and its supernatant was recovered. After a protein concentration was measured using Nano Drop (manufactured by Thermo Scientific, Inc.), the protein concentration was adjusted to 500 ng/μL. Subsequently, the amount of Muc5ac included in the protein solution prepared was quantified using the same ELISA assay as in Example 1. The results are shown in FIG. 4b. The amount of Muc5ac protein in the conjunctival tissue collected from the Compound 1 administration group was approximately equal to that of the control group. This result is combined with the results that the amount of Muc5ac secreted from the tissue of the Compound 1 administration group was remarkably high, and together demonstrates that Compound 1 has an action of enhancing synthesis and secretion of mucin.

Further, the conjunctival tissues from the control group and the administration group were subjected to PAS staining, which stains neutral polysaccharides and glycoproteins. Specifically, a conjunctival tissue was collected from a rabbit; the conjunctive tissue collected was cut into regions at the upper, nasal, lower, and ear sides; and paraffin sections were prepared. Next, after washed with distilled water for deparaffinization, the sections were immersed in 3% acetic acid aqueous solution and soaked in an alcian blue solution for 30 minutes. After washed with distilled water, the sections were soaked in 1% periodic acid aqueous solution for 10 minutes, washed with running water for 5 minutes, and washed with distilled water. After soaked in a cold Schiff reagent for 10 minutes, the sections were soaked in sulfurous acid solution for 3 minutes and subjected to sulfurous acid solution treatment. After this treatment was repeated 3 times, the sections were washed with running water for 5 minutes and soaked for 3 to 5 minutes in a Mayer's hematoxylin solution, which stained cell nuclei. After washed with running water for 10 minutes for coloring, the sections were subjected to dehydration and clearing treatment, followed by sealing. The sections were observed using a microscope, and photographed.

The results are shown in FIG. 5. The amount of Muc5ac (stained red-purple) in the conjunctival tissue from the Compound 1 administration group was apparently lower than that of the control group. This indicates that in the Compound 1 administration group, Muc5 ac is not retained inside a cell, but is secreted outside the cell; and Compound 1 enhances secretion of mucin.

The invention claimed is:

1. A method for preventing or treating dry eye, comprising administering to a patient suffering from dry eye a pharmaceutical composition consisting of an effective amount of cyclo-trans-4-L-hydroxyprolyl-L-serine as an active ingredient and at least one pharmaceutically acceptable additive.

2. A method for preventing or treating dry eye caused by a decrease in an amount of mucin, comprising administering to a patient suffering from dry eye caused by a decrease in an amount of mucin a pharmaceutical composition consisting of an effective amount of cyclo-trans-4-L-hydroxyprolyl-L-serine as an active ingredient and at least one pharmaceutically acceptable additive.

3. A method for enhancing mucin secretion, comprising administering to a patient suffering from a decrease in mucin secretion a pharmaceutical composition consisting of an effective amount of cyclo-trans-4-L-hydroxyprolyl-L-serine as an active ingredient and at least one pharmaceutically acceptable additive.

4. A method for enhancing repair of ocular tissue damage caused by dry eye, comprising administering to a patient suffering from ocular tissue damage caused by dry eye a pharmaceutical composition consisting of an effective amount of cyclo-trans-4-L-hydroxyprolyl-L-serine as an active ingredient and at least one pharmaceutically acceptable additive.

* * * * *